(12) United States Patent
Zhang et al.

(10) Patent No.: US 7,780,841 B2
(45) Date of Patent: Aug. 24, 2010

(54) E-FIELD INDUCED ION SELECTIVE MOLECULAR DEPOSITION ONTO SENSOR ARRAYS

(75) Inventors: Sean Xiao-An Zhang, Cupertino, CA (US); Zhiyong Li, Palo Alto, CA (US); Zhang-Lin Zhou, Mountain View, CA (US); William M. Tong, San Francisco, CA (US); R. Stanley Williams, Portola Valley, CA (US); Yong Chen, Sherman Oaks, CA (US)

(73) Assignee: Hewlett-Packard Development Company. L.P., Houston, TX (US)

( * ) Notice: Subject to any disclaimer, the term of this patent is extended or adjusted under 35 U.S.C. 154(b) by 1252 days.

(21) Appl. No.: 11/059,258

(22) Filed: Feb. 15, 2005

(65) Prior Publication Data

US 2006/0180480 A1 Aug. 17, 2006

(51) Int. Cl.
*G01N 27/327* (2006.01)
(52) U.S. Cl. .............................. 205/777.5; 204/403.01
(58) Field of Classification Search ................................
204/403.01–403.15, 416–418; 205/777.5, 205/778, 792
See application file for complete search history.

(56) References Cited

U.S. PATENT DOCUMENTS 5,066,372 A * 11/1991 Weetall ........................ 506/4
5,250,163 A * 10/1993 Epstein et al. ........... 205/777.5
5,264,104 A * 11/1993 Gregg et al. ........... 204/403.09
5,352,574 A * 10/1994 Guiseppi-Elie ................ 435/4
6,458,600 B1 * 10/2002 Mirsky et al. ................ 436/518

OTHER PUBLICATIONS

Lindfors et al. "All-solid-state calcium-selective electrode prepared of soluble electrically conducting polyaniline and di(2-ethylhexyl)phosphate with ETH1001 as neutral carrier," Analytica Chemica Acta 404.*
Karami et al., "Dodecyl benzene sulfonate anion-selective electrode based on polyaniline-coated electrode," Talanta 63 (2004) 743-749.*
IUPAC definition of "chemical adsorption" downloaded from www.iupac.org on Jul. 9, 2009.*

* cited by examiner

*Primary Examiner*—Alex Noguerola
(74) *Attorney, Agent, or Firm*—David W. Collins

(57) ABSTRACT

A sensor array for sensing at least one of chemical moieties and biological moieties is provided. The sensor array comprises a plurality of working electrodes electrically associated with a reference electrode, each working electrode in combination with the reference electrode forming a transducer. Each working electrode is provided with a coating of a sensing element comprised of an ionizable moiety and a functional group sensitive to one of the chemical and/or biological moieties.

28 Claims, 5 Drawing Sheets

E-FIELD INDUCED ION SELECTIVE MOLECULAR DEPOSITION ONTO SENSOR ARRAYS

CROSS-REFERENCE TO RELATED APPLICATION

The present application is related to application Ser. No. 11/059,430, filed on even date herewith, the contents of which are incorporated herein by reference, now abandoned. That application relates to a method for integrating a certain array of selected chemical differentiators in conjunction with certain transducers to form a system capable of recognizing a board spectrum of analytes.

TECHNICAL FIELD

The present invention is directed to sensor arrays for detection of various chemical and/or biological species.

BACKGROUND ART

The characterization and quantification of individual chemical and complex biological molecules is extremely important in fields such as medicine, environmental protection, security, military, and other areas. The determination of individual chemical and complex biological molecules is currently complex and generally requires sophisticated and bulky equipment.

Even though many commercial products along with hundreds of patents have been filed in chemical and biological sensor field, sensor technologies to date are generally used to detect a single type or very few different types of molecules. None of them are particularly adapted to allow a very large number of different types of chemical or biological molecules to be detected.

In order to develop a highly selective, highly sensitive, and universal sensor system, a micro- or nano-sensor array with multiple different sensing elements, each connected to its own specific transducer, has been regarded as one of the possible ultimate solutions. Sensor arrays offer several advantages over single sensors. For example, sensor arrays have better sensitivity to a wider range of analytes. Such arrays offer better selectivity, multi-component analysis, and analyte recognition, rather than mere detection. Sensor arrays are more analogous to olfaction systems containing multiple receptors, whose responses are interpreted by neuron odor recognition processes.

Many existing technologies can be used to build a normal or mini scale of sensor arrays with multiple different sensing elements; examples of such technologies include e-beam lithography, selective thermo deposition, etc. However, none of the above-mentioned technologies work well in the micro- or nano-region. Selectively introducing different types of sensing elements onto different transducers in the micro- or nano-region and providing the micro- or nano-sensor array with multiple different sensing elements have been under active investigation. However, actually achieving these goals has been a challenge, due to the difficulties associated with how to selectively introduce different types of sensing elements onto different transducers in the micro- or nano-region.

Thus, there is a need for different types of sensing elements on different transducers, as well as sensor arrays with multiple different sensing elements, both in the micro- and nano-regimes.

DISCLOSURE OF INVENTION

A sensor array for sensing at least one of chemical moieties and biological moieties is provided. The sensor array comprises a plurality of working electrodes electrically associated with a reference electrode, each working electrode in combination with the reference electrode forming a transducer. Each working electrode is provided with a coating of a sensing element comprised of an ionizable moiety and a functional group sensitive to one of the chemical and biological moieties.

A method of forming the sensor array is provided. The method comprises:
 providing a plurality of working electrodes;
 providing a reference electrode electrically associated with the plurality of working electrodes, each working electrode in combination with the reference electrode forming a transducer; and
 providing each working electrode provided with a coating of a sensing element comprised of an ionizable moiety and a functional group sensitive to one of the chemical and biological moieties.

A method of sensing at least one of chemical moieties and biological moieties is provided. The method comprises:
 providing a sensor array, said sensor array comprising a plurality of working electrodes electrically associated with a reference electrode, each working electrode in combination with said reference electrode forming a transducer, each working electrode provided with a coating of a sensing element comprised of an ionizable moiety and a functional group sensitive to at least one said chemical and biological moiety;
 exposing said sensor array to at least one chemical moiety or biological moiety or both; and
 detecting a signal corresponding to a sensed chemical moiety or biological moiety or both.

BEST MODES FOR CARRYING OUT THE INVENTION

Figure 1:
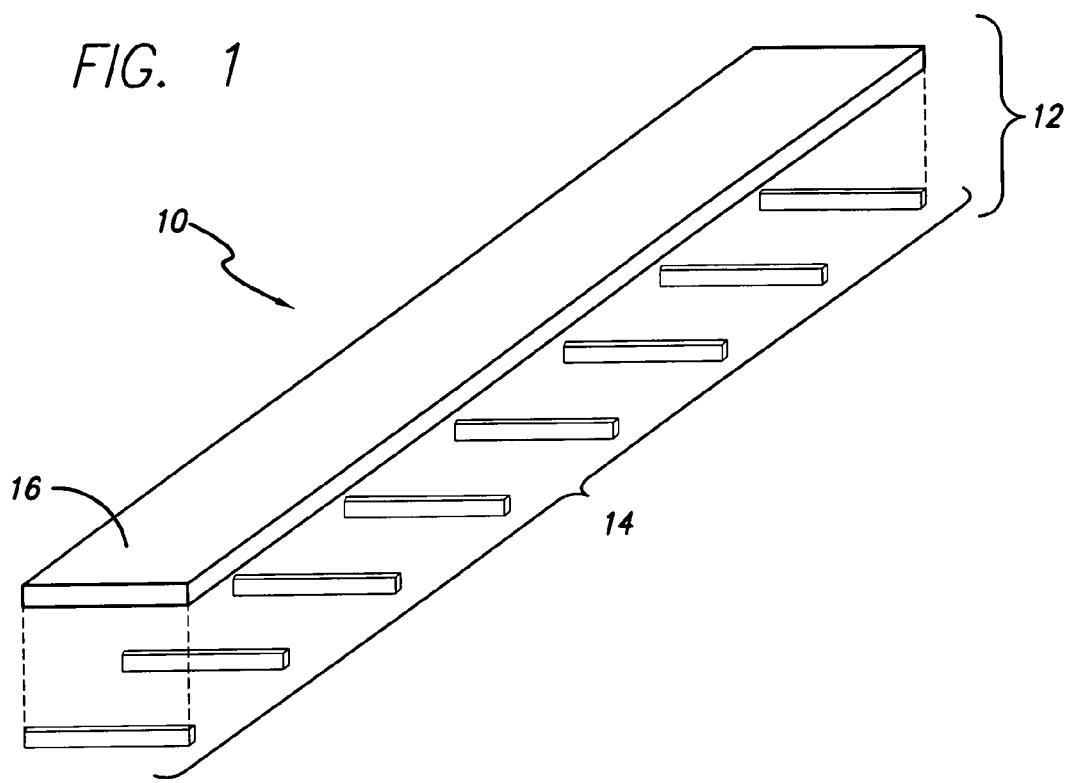
FIG. 1 depicts a basic structure of an array of transducers employed in the practice of the embodiments.

Reference is made now in detail to specific embodiments, which illustrates the best mode presently contemplated by the inventors for practicing the invention. Alternative embodiments are also briefly described as applicable.

As used herein, the term "micro-regime" refers to 0.5 μm and above.

As used herein, the term "nano-regime" refers to 1 to 100 nm.

In accordance with the teachings herein, an electric field (E-field) directed ion-selective molecular deposition process is provided. Basically, different sensing elements are introduced selectively onto different transducers (whether through chemical bonding or physical adsorptions) by selectively activating the particular transducer (electrode) in an array and deactivating the rest of the transducers. The activation is achieved by manipulation of the electric field among the array of the transducers (electrodes). The sensing elements are provided with an ionizable connecting group. This is done by pre-ionizing each particular type of sensing element, and then introducing the sensing element into the system containing one or more selectively activated micro- or nano-transducer(s) in the array.

Examples of methods for pre-ionization include, but are not limited to, electrospray and chemical ionization. The former pre-ionization method has been used in mass-spectrometer instruments. The van der Waals interaction between the pre-ionized sensing elements and the E-field system in the array will direct the ion-selective deposition very precisely and highly selectively. The positive potential on the activated electrode will attract the negatively charged sensing elements onto its (or their) surface and promote chemical bonding reaction between them. The negative potential on those deactivated transducers (electrode) in the system will repel those anionic sensing elements away from their surface and protect themselves from unwanted deposition. Through this type of sequential activation and deposition process, a micro- or nano-sensor array with multiple different sensing elements, each connected to its own specific transducer, is easily achieved.

The ionizable moiety may be electrophilic. Examples of suitable electrophilic moieties include, but are not limited to, $-NH_2^+$, $-NHR^+$, $-NR_2^+$, cyclic amine salts, pyridine salts, substituted pyridine salts, $PH_2^+$, $-PHR^+$, $-PR_2^+$, etc. The R groups are conventional functional groups, such as alkyl, aryl, acyl, etc.

Alternatively, the ionizable moiety may be nucleophilic. Examples of suitable nucleophilic moieties include, but are not limited to, $-S^-$, $-O^-$, $-NH^-$, $-N(alkyl)^-$, $-N(aryl)^-$, $N(acyl)^-$, $-COO^-$, $-C(=S)O^-$, $-C(=S)S^-$, $-C(=O)S^-$, $-P(=O)O_2^-$, $-P(=O)O_2H^-$, $-S(=O)_2O^-$, etc.

FIGS. 1-5 offer a schematic overview of the principles and design characteristics of how this process works with a generic example, while a schematic overview on a more specific example with actual chemical functional groups is given in FIGS. 6-9. It is worth noting that all of the examples described below use nucleophilic anions (Nu⁻) as the preferred method to covalently link the sensing elements to the transducer surface. However, other linking means are possible even though they are not explicitly given here. For example, one might use electrophilic cations (E⁺) to link in either covalent bonding or ionic bonding to the surface of an activated transducer, and the activated transducer should have a negative potential and the deactivated working electrode will have the positive potential in this situation.

All the examples herein are only illustrative of the preferred embodiment, which achieves the objects, features and advantages of present teachings, and it is not intended that the present teachings be limited thereto.

The following legends and explanatory notes apply to FIGS. 1-5:

The symbol Nu⁻ is an abbreviation for an anionic nucleophilic terminating group, which is capable of self-assembly onto the selected solid substrate (transducer). It is generated chemically or electrochemically from an anionic functional group. It is worth noting that those anionic functional groups used here should be chemically inert or have very low reactivity towards the surface of transducers, but at the same time, their anionic forms should be highly reactive and much more reactive than other type of anions existed in the system. The Nu⁻ can be, but is not limited to, one of the following: $-S^-$, $-O^-$, $-NH^-$, $-N(alkyl)^-$, $-N(aryl)^-$, $N(acyl)^-$, $-COO^-$, etc.

$FG_1$, $FG_2$, $FG_3$, $FG_4$, $FG_5$, $FG_6$, $FG_7$, and $FG_8$ are abbreviations for different sensing functional end-groups. They can be the same or different. Those functional groups can be either neutral or ionizable during the pre-ionization process. However, these sensing functional end-groups should not interfere or compete with Nu⁻ during the E-field directed ion selective molecular deposition process. On the contrary, these sensing functional end-groups should form certain linkages easily with the molecules to be detected after the sensor system is activated. The sensing functional end-groups can be, but are not limited to, any one of the following: SH, OH, $NH_2$, NH-alkyl, NH-aryl, NH-acyl, unsaturated hydrocarbon or substituted hydrocarbon, heterocyclic systems, carboxylic acid or its derivatives (e.g., ester or amide, etc.), sulfuric acid or its derivatives (e.g., ester or amide, etc.), and phosphoric acid or its derivatives (e.g., ester or amide, etc.). It is worth noticing that even though only $FG_1$, $FG_2$, $FG_3$, $FG_4$, $FG_5$, $FG_6$, $FG_7$, and $FG_8$ are given here, more or fewer of other types of sensing elements can be used, depending on the specific application (e.g., using a specific enzyme, protein, bioactive or biospecific molecule, combination of certain chromophore or fluorophore with the sensing molecule to detect the fluorescent change or color change, etc.).

The working electrodes here represent different types of E-field activatable transducers in the array. They are made of a single metal, metal alloy, metal oxide, organic-semiconducting material, or inorganic-semiconducting material, etc. The working electrodes are designed in such way that at least one of their surfaces has certain properties and can form some kind of strong linkage with Nu⁻. The linkage between Nu⁻ and working electrodes can be either a chemical bonding or a physical adsorption, even though covalent linkage of the sensing elements to the transducer surface is preferred here. A special surface treatment of the working electrode may be needed in order to form a good covalent linkage with the sensing elements. For example, one can either (a) coat a thin layer of novel metal (e.g., Pt, Au, Ag, Cu, etc.) on the top of the working electrode, which can form a strong covalent bond with $-S^-$ or $-NH^-$, etc.; or (b) cauterize and halogenate of the surface of $SiO_2$, in which case, the resulting Si—X (X=Cl, Br, I) functional group on the surface of the working electrode will be highly reactive with many anionic nucleophiles to form a strong covalent bond through a nucleophilic substitution.

The reference electrode depicted in the Figures is a supporting electrode. It is chemically inert toward the anionic nucleophiles. The function of the reference electrode here is to form electrode pairs with at least some of the working electrodes and provide an adequate E-field with them. It helps to deactivate those working electrodes during a sequential E-field directing molecular deposition process and prevents them from unwanted molecular deposition during the selective deposition process.

It is worth noting that more or less of other type of anions usually exist in the system, depending on which method is used to generate the anionic sensing element(s). The solvent and the reagent used in this process (usually a stronger base in the chemical ionization process) must be carefully selected in order to ensure a smooth and quantitative generation of the anion of the sensing elements without introducing other types of anions in the system. In the case that there might be still trace amount of other anions in the system due to certain processes, for example, some excess reagent remaining from the chemical ionization reaction, the reagent should be chosen with a desired property that it is a strong base and poor nucleophile, so that it can deprotonate the sensing element easily and react with the surface of transducer much slowly.

FIG. 1 depicts a structure comprising an array 10 of transducers 12. The transducers comprise a plurality of working electrodes 14 electrically associated with a reference electrode 16.

Figure 2:
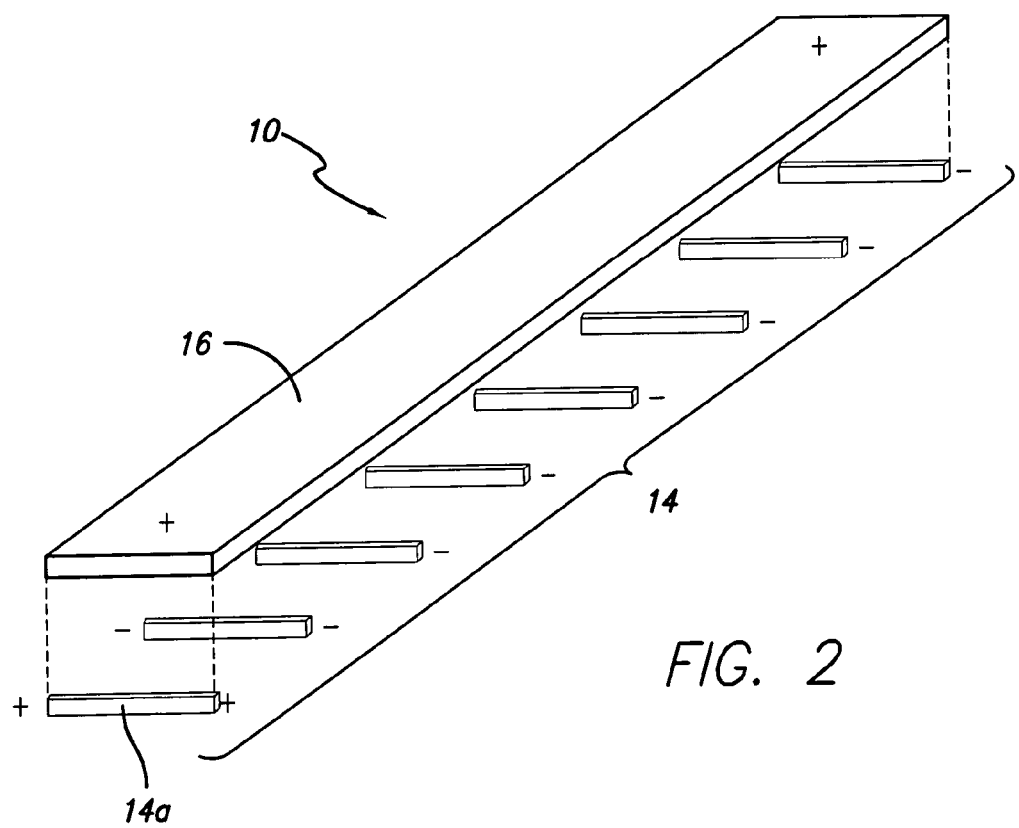
FIG. 2 depicts selective activation of one of the working electrodes (transducers) of FIG. 1, while deactivating the others.

As depicted in FIG. 2, only one of the working electrodes, 14a, along with the reference electrode 16, is activated by applying a positive potential on both the selected working electrode and the reference electrode, while the rest of the working electrodes 14 in the array 10 are deactivated by applying a negative potential on them at the same time.

Figure 3:
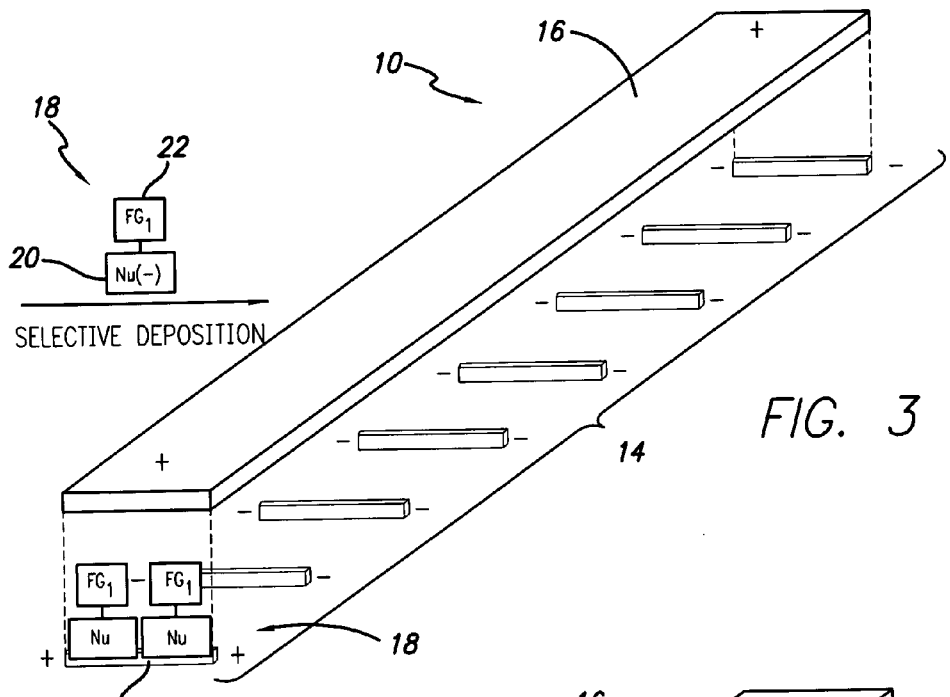
FIG. 3 illustrates the selective deposition of pre-ionized sensing elements onto the activated transducer (electrode) of FIG. 2.

As depicted in FIG. 3, a first type of sensing element 18, comprising a nucleophilic moiety $Nu^-$ 20 and a functional group $FG_1$ 22 is provided. The sensing element initially comprises a moiety that is anionizable to nucleophilic moiety plus the functional group. The anionizable moiety is then anionized chemically or electrochemically, and the sensing element is introduced into the system 10 with only one activated working electrode 14a. The positive potential on the activated working electrode 14a attracts the negatively charged sensing elements 18 onto its surface and form a covalent linkage with them through nucleophilic substitution. The negative potential on those deactivated electrodes 14 in the array 10 drives the anionized sensing elements 18 away from their surface with the help of the reference electrode 16, and protects them from unwanted deposition. This process is very selective and essentially no undesired molecular deposition takes place. A post-cleaning step is used to avoid cross-contamination and make the system ready for next type of molecular deposition. The so-called post-cleaning step is intended to sweep out those loosely attached ionic molecular species from the surface of the reference electrode 16 by using certain appropriate media (solvent or gas) or vacuum while temporarily removing the potential on the reference electrode 16. In this way, the excess reagents from previous deposition processes are removed and cross-contamination to the next sensor element deposition is avoided.

Figure 4:
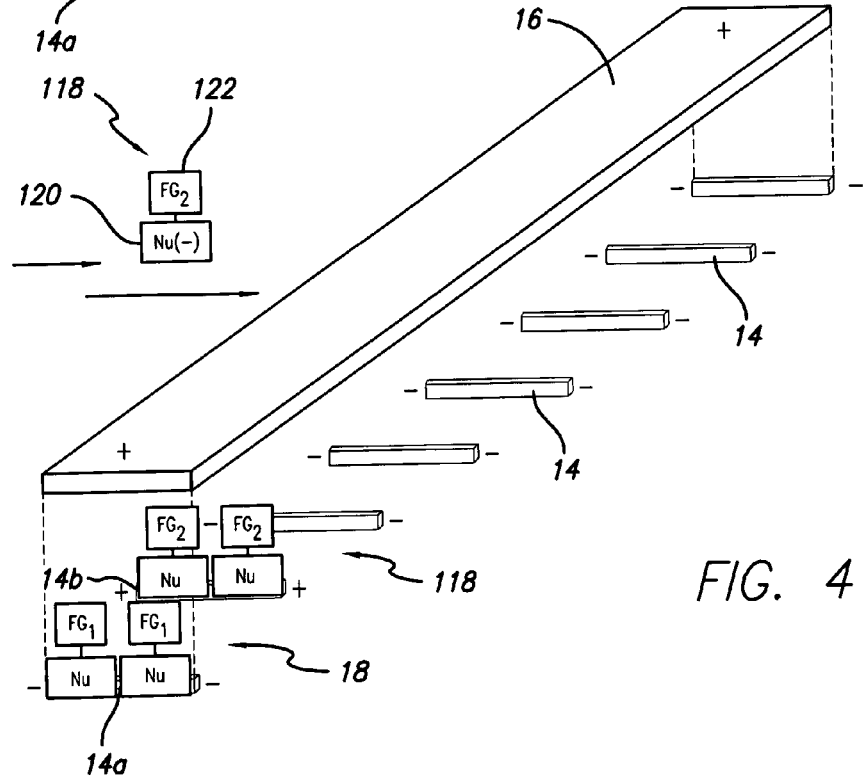
FIG. 4 illustrates the selective deposition of a second type of sensing elements onto the transducer.

As depicted in FIG. 4, a second type of sensing element 118 is deposited selectively onto a second working electrode 14b by the four-step process of selective activation of the second electrode, pre-ionization of the second type of sensing elements, E-field directed deposition, and post-cleaning. The sensing element 118 comprises a nucleophilic moiety $Nu^-$ 120 and a functional group $FG_2$ 122.

Figure 5:
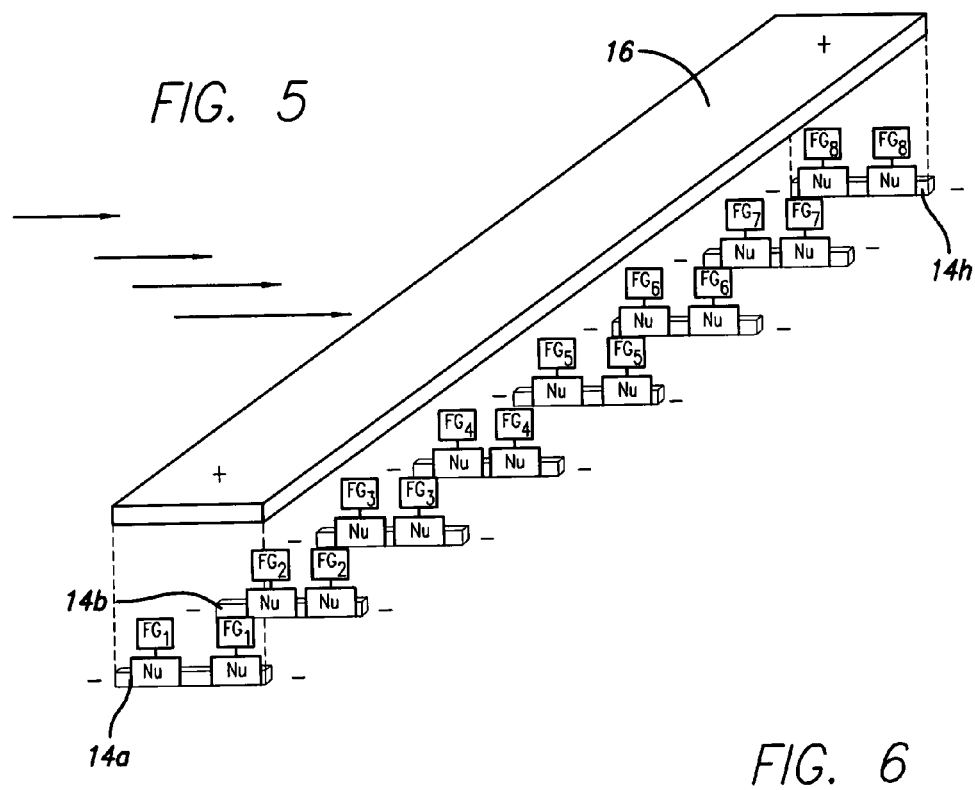
FIG. 5 illustrates the selective deposition of different types of sensing elements sequentially onto the different transducers in the array.

As depicted in FIG. 5, by repeating the four-steps process (selective activation of a working electrode 14, pre-anionization of another type of sensing element, E-field directed deposition, and post-cleaning) sequentially on the different working electrodes to provide a sequence of electrodes 14a ... 14h, different types of sensing elements can be deposited very selectively onto different working electrodes (transducers) in the array 10.

A more specific example of E-field directed ion selective molecular deposition with actual chemical functional groups is given in FIGS. 6-9.

In this particular example, $S^-$ is chosen as a preferred anionic nucleophile 20. The alkyl amine, carboxylic acid, aryl amine, phenol, amide, OH, aromatic or aliphatic ending groups are chosen here as desired sensing groups 22. It is worth noticing that even though the examples described here use $-NR_2$, $-COOH$, $-CONH2$, $-Ar-NH2$, $-ArOH$, $-Ar$, $-R$, $-OH$, etc. as preferred sensing groups, other type means are possible even though they are not explicitly given here. All the examples are only illustrative of the preferred embodiment, which achieves the objects, features and advantages of present teachings, and it is not intended that the present teachings be limited thereto.

In this particular example, the surface of working electrodes 14 can either be made of noble metal (such as Au, Pt, Ag, Cu, etc.) or Si—Cl (if using a Si electrode). Other materials useful for working electrodes include, but are not limited to, GaAs, InP, $In_2O_3$, and ZnO. The reference electrode 16 can be made of any material that is chemically inert material to $S^-$; examples include, but are not limited to, Si, C, TiN, ITO (indium tin oxide), and ZnO. If a different anionic nucleophile is used in place of $S^-$, then the reference electrode 16 would comprise a material inert to that different anionic nucleophile. The determination of a suitable reference electrode material is readily within the ability of the person skilled in the art, and would require no undue experimentation.

At first, a desired array of working electrodes 14 and reference electrode 16 are prepared, and pretreated to possess certain desired chemical properties (which can form a covalent linkage with $S^-$ through chemical reaction). Then, one of the working electrodes 14a is selectively activated by applying a positive potential on it and deactivating the other working electrodes in the array 10 with a negative potential, as described above with reference to FIG. 1.

Figure 6:
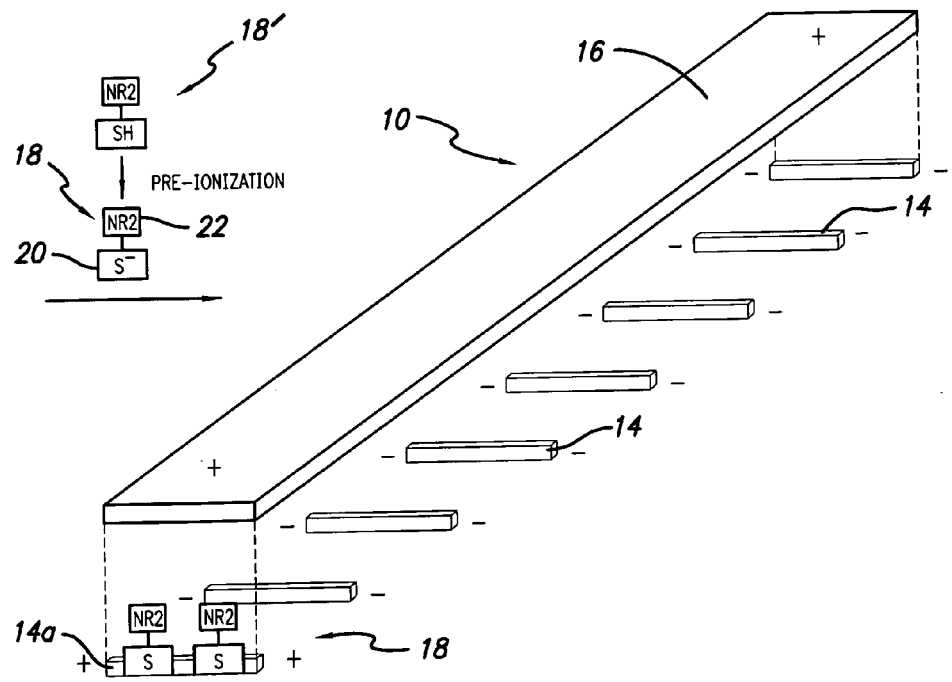
FIGS. 6-9 depict the same sequence of process steps as FIGS. 1-5, but for a specific set of chemical functional groups.

As depicted in FIG. 6, the thiol group 20 of amine-terminated ($-NR_2$) sensing elements 18' is first pre-anionized chemically or electrochemically to strip off the hydrogen atom from the thiol group ($-SH$), leaving $S^-$. Then the ionized sensing element 18 is introduced into the system with only one activated working electrode 14a in the array 10. The positive potential on the activated working electrode 14a attracts the negatively charged sensing elements 18 onto its surface and forms a covalent linkage with them through nucleophilic substitution. The negative potential on those deactivated electrodes 14 in the array 10 drives the anionized sensing elements 18 away from their surface with help from the reference electrode 16, and protects them from unwanted deposition. This process is very selective and essentially no undesired molecular deposition takes place. A post-cleaning step is necessary to avoid cross-contamination and make the system ready for next type of molecular deposition. The so-called post-cleaning step is to sweep out those loosely attached ionic molecular species from the surface of reference electrode by using certain proper media (solvent or gas) or vacuum while temporarily removing the potential on the reference electrode.

In the amine, R is an atom or functional group. It can be a hydrogen atom or an alkyl group. A methyl or ethyl group is preferred in some embodiments. The two R moieties may be the same or different.

Figure 7:
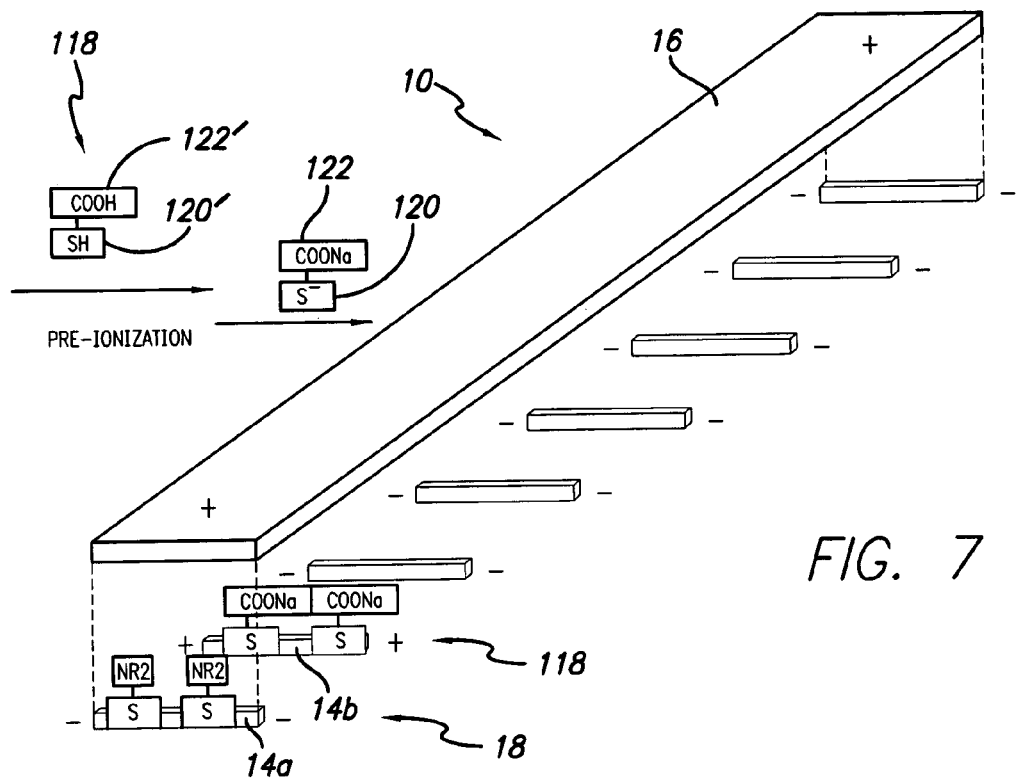

As depicted in FIG. 7, a second type of sensing element 118 is a dual functional molecule with carboxylic acid functional end-group 122' and thiol ($-SH$) group 120'. The sensing element 118 is deposited selectively onto a second working electrode 14b by a four-steps process (selective activation of the second electrode, pre-ionization of the second type of sensing element, E-field directed deposition, and post-cleaning). Under chemical anionization, $-COOH$ is anionized to form $-COONa$ 122, and the $-SH$ is anionized also to form $-SNa$ ($S^-$) 120 for example, by NaOH treatment. In the case of using a silicon electrode 14b, even though both its carboxylic acid (—COOH) and thiol (—SH) group can be anionized at the same time under the reaction condition, however the nucleophilicity of the —S⁻ portion of the resulting anionized specie is much stronger than its —COO⁻ portion and consequently, the rate of nucleophilic substitution of Cl at the Si—Cl site with S⁻ anion is 3 to 4 orders faster than the corresponding —COO⁻ anion. This results in exclusively an —S—Si moiety bonded to the bottom electrode, while the anionized carboxylic acid functional end-group remains unbonded. The desired S-attachment is the dominant product from the process. In the case of using noble metal electrodes 14, only the S⁻ can react with the noble metal to form a strong covalent linkage, and the —COO⁻ group is totally inert in this situation.

Figure 8:
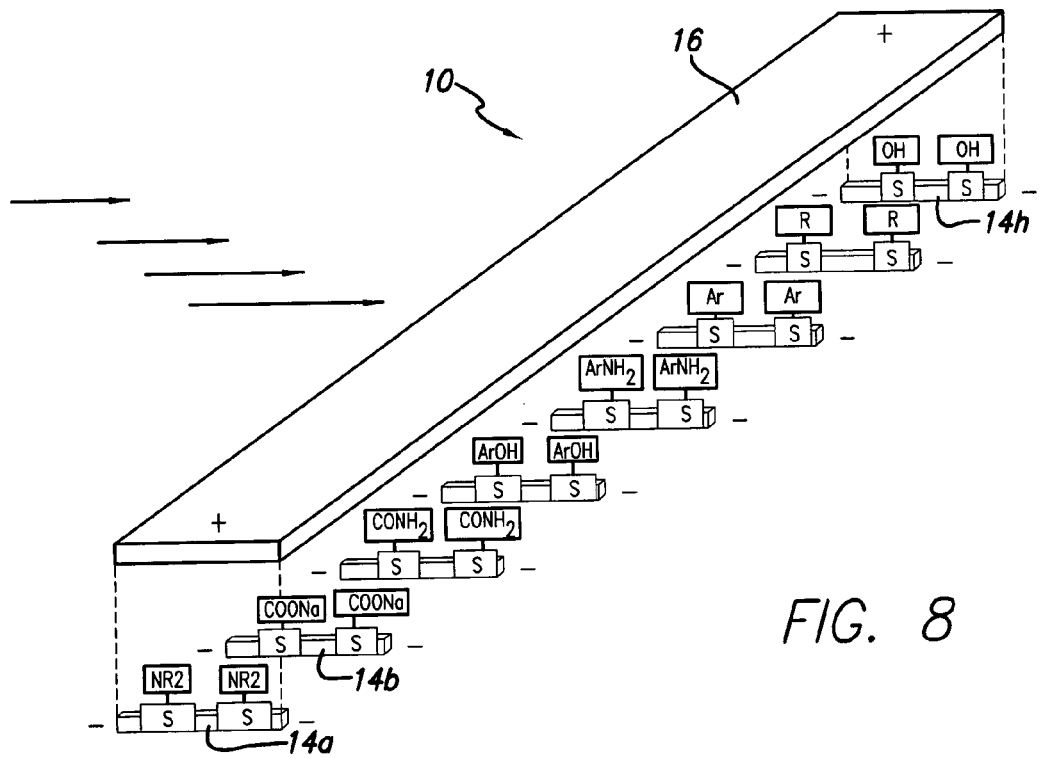

As depicted in FIG. 8, by repeating the four-steps process (selective activation of the next electrode, pre-anionization of the next type of sensing element, E-field directed deposition, and post-cleaning) sequentially on the different working electrodes, various types of sensing elements can be deposited very precisely and selectively onto different working electrodes (transducers) in an array.

Figure 9:
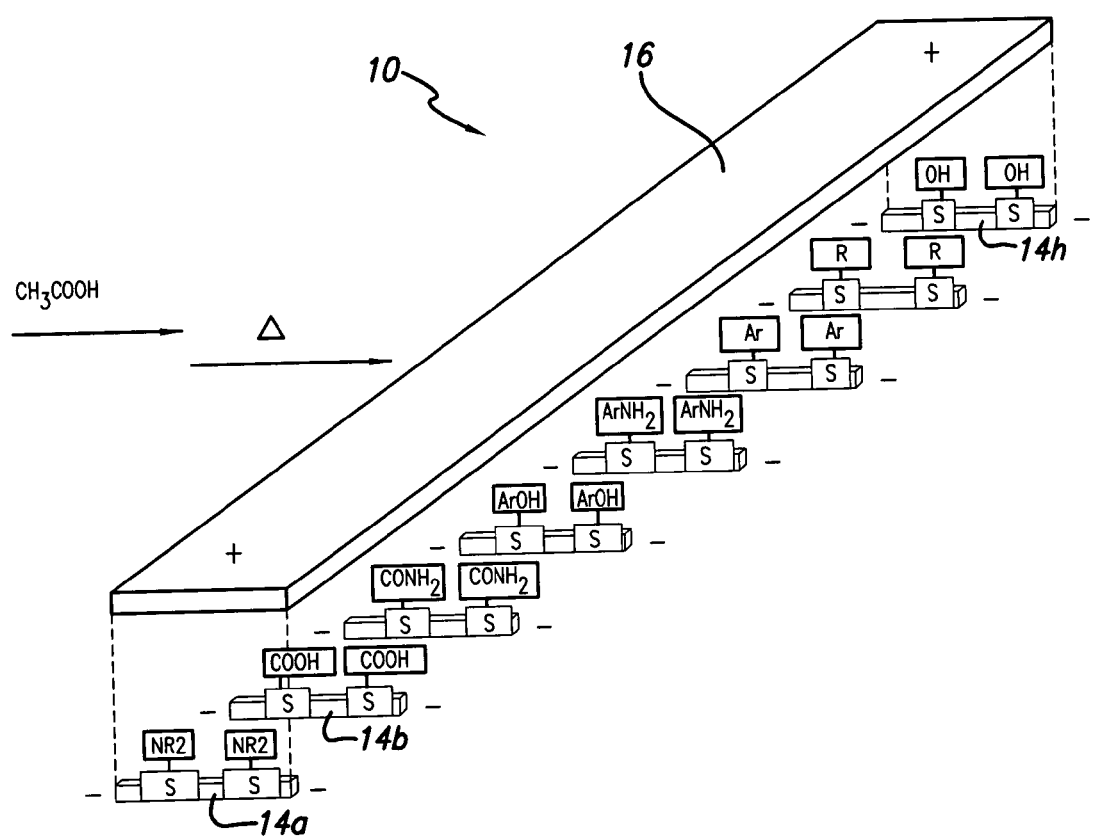

Since the —COONa group may not be a good sensing group in some instances, it may be necessary to convert the —COONa group to the corresponding —COOH group by a two-steps post-treatment process (acidification followed by heat treatment) to activate the sensor system, as shown in FIG. 9, at electrode 14b.

It can be seen from the Table below that each specific sensing element can detect a range of molecular functional groups based on their specific oriented chemical or physical interactions. However, different functional groups will usually interact with a unique sub-set of the sensing elements in the sensor array. While eight sensing elements are shown in the Figures, it will be appreciated that more or less than that number may be actually employed in a working device. This characteristic signature when combined with the knowledge of its molecular backbone and molecular mass will enable identification of the analyte in most cases. While chemical moieties are specifically disclosed, it will be appreciated that the techniques disclosed herein of electric field induced selective deposition of sensor arrays can be used for biomolecular sensor arrays as well.

TABLE

Chemical Functional Group Sensing Elements

| Sensing element [Specific example] | Target functional group | Specific examples of functional groups being detected | Unit (or molecular) mass | Notes |
|---|---|---|---|---|
| Stronger acid (SA) [—CF$_2$CO$_2$H] | Stronger and weaker base | —NH—NR$_1$R$_2$<br>—NR$_1$R$_2$<br>—NR$_1$R$_2$<br>—NH(C=NH)NR$_1$R$_2$<br>pyridine or its alkyl substituents<br>amino-pyridine or its substituents<br>imidazole or its alkyl substituents<br>pyrrole or its alkyl substituents | 31 + 14 n<br>16 + 14 n<br>92 + 14 n<br>58 + 14 n<br>79 + 14 n<br>94 + 14 n<br>68 + 14 n<br>67 + 14 n | n (the number of carbon atoms in each molecular functional group) = 0, 1, 2, 3, . . .<br>R$_1$ = H or alkyl<br>R$_2$ = H or alkyl |
| Weaker acid (WA) [φ-OH] | Stronger base or hydrogen bonding accepting group | —NH—NR$_1$R$_2$<br>—NR$_1$R$_2$<br>—NH(C=NH)NR$_1$R$_2$<br>imidazole or its alkyl substituents<br>amino-pyridine or its substituents<br>—CN<br>—C(=O)R$_1$<br>—NO$_2$<br>—C(=O)NHR$_1$ | 31 + 14 n<br>16 + 14 n<br>58 + 14 n<br>68 + 14 n<br>94 + 14 n<br>26<br>29 + 14 n<br>46<br>44 + 14 n | n (the number of carbon atoms in each molecular functional group) = 0, 1, 2, 3, . . .<br>R$_1$ = H or alkyl<br>R$_2$ = H or alkyl |
| Stronger base (SB) [-Alkyl-NR$_1$R$_2$] | Stronger and weaker acid | —CO$_2$H<br>—PO$_3$H$_2$<br>—B(OH)$_2$<br>φ-OH<br>φ-SH | 45<br>81<br>45<br>93 + 14 n<br>109 + 14 n | n (the number of carbon atoms in each molecular functional group) = 0, 1, 2, 3, . . . |
| Weaker base (WB) [-φ-NH$_2$] | Stronger acid or hydrogen bonding accepting group | —CO$_2$H<br>—PO$_3$H$_2$<br>—CN<br>—C(=O)R$_1$<br>—NO$_2$<br>—C(=O)NHR$_1$ | 45<br>81<br>26<br>29 + 14 n<br>46<br>44 + 14 n | |
| Hydrogen bonding accepting group (HBAG) [—CO—NR$_1$R$_2$] | Hydrophilic group | —OH<br>—SH<br>—NH$_2$<br>—NH(C=NH)NR$_1$R$_2$<br>pyrrole or its alkyl substituents<br>imidazole or its alkyl substituents | 17<br>33<br>16<br>58 + 14 n<br>67 + 14 n<br>68 + 14 n | R$_1$ = H or alkyl<br>R$_2$ = H or alkyl<br>n [the number of carbon atoms in the alkyl group(s)] = 0, 1, 2, 3, . . . |
| Hydrophilic group (HIG) [—OH] | Hydrogen bonding accepting group | —NH—(C=NH)—NR$_1$R$_2$<br>—CN<br>—C(=O)R$_1$<br>—NO$_2$<br>—C(=O)NHR$_1$ | 58 + 14 n<br>26<br>29 + 14 n<br>46<br>44 + 14 n | n [the number of carbon atoms in the alkyl group(s)] = 0, 1, 2, 3, . . .<br>R$_1$ = H or alkyl |

Note:
φ = phenyl (—C$_6$H$_5$)

The current teachings provide a simple solution on how to selectively introduce different types of sensing elements onto different transducers in the micro- or nano-region. The teachings permit construction of a micro- or nano-sensor array of multiple different sensing elements.

The teachings disclosed herein permit building a highly selective and universal micro- or nano-sensing system, which will allow a very large number of different types of chemical or biological molecules to be detected in a simple, fast, and cost effective way.

INDUSTRIAL APPLICABILITY

The sensor array is expected to find use in detecting various chemical and/or biological species.

What is claimed is:

1. A sensor array for sensing a plurality of detectable functional groups associated with at least one of chemical moieties and biological moieties on a single molecule, said sensor array comprising:
a plurality of working electrodes electrically associated with a single reference electrode, each working electrode forming a transducer, each working electrode provided with a coating of a sensing element comprised of an ionized moiety and a sensing functional group sensitive to at least one of said chemical and biological moieties, each coating sensitive to a different detectable functional group;
wherein each of the plurality of working electrodes is configured to be deactivated, after having been previously activated, during activation of an other of the plurality of working electrodes and deposition of the coating on the other of the plurality of working electrodes, such that each working electrode is configured to be coated one electrode at a time.

2. The sensor array of claim 1 wherein said ionized moiety is electrophilic.

3. The sensor array of claim 2 wherein said electrophilic moiety is selected from the group consisting of $-NH_2^+$, $-NHR^+$, $-NR_2^+$, cyclic amine salts, pyridine salts, substituted pyridine salts, $PH_2^+$, $-PHR^+$, and $-PR_2^+$.

4. The sensor array of claim 1 wherein said ionized moiety is nucleophilic.

5. The sensor array of claim 4 wherein said nucleophilic moiety is selected from the group consisting of $-S^-$, $-O^-$, $-NH^-$, $-N(alkyl)^-$, $-N(aryl)^-$, $N(acyl)^-$, $-COO^-$, $-C(=S)O^-$, $-C(=S)S^-$, $-C(=O)S^-$, $-P(=O)O_2^-$, $-P(=O)_2H^-$, and $-S(=O)_2O^-$.

6. The sensor array of claim 1 wherein said sensing functional group is selected from the group consisting of SH, OH, $NH_2$, NH-alkyl, NH-aryl, NH-acyl, unsaturated hydrocarbon or substituted hydrocarbon, heterocyclic systems, carboxylic acid and its derivatives, sulfuric acid and its derivatives, and phosphoric acid and its derivatives.

7. The sensor array of claim 1 wherein each working electrode is independently selected from the group consisting of single metals, metal alloys, metal oxides, organic-semiconducting materials, and inorganic-semiconducting materials.

8. The sensor array of claim 7 wherein each working electrode is selected from the group consisting of Pt, Au, Ag, Cu, Si, GaAs, InP, $In_2O_3$, and ZnO.

9. The sensor array of claim 1 wherein said reference electrode forms electrode pairs with at least some of said working electrodes and is chemically inert toward said ionized moiety.

10. A method of forming a sensor array for sensing a plurality of detectable functional groups associated with at least one of chemical moieties and biological moieties on a single molecule, said method comprising:
providing a plurality of working electrodes;
providing a single reference electrode electrically associated with said plurality of working electrodes, each working electrode forming a transducer; and
selectively depositing a coating on each working electrode, the coating including a sensing element comprised of an ionized moiety and a sensing functional group sensitive to at least one of the chemical and biological moieties on the single molecule, each coating sensitive to a different detectable functional group, each coating provided by performing an electric-field directed deposition of said sensing element onto said electrode;
wherein the selective deposition of the coating on each working electrode is accomplished via one electrode at a time by activating one working electrode to be coated while deactivating each other of the working electrodes.

11. The method of claim 10 wherein said ionized moiety is electrophilic.

12. The method of claim 11 wherein said electrophilic moiety is selected from the group consisting of $-NH_2^+$, $-NHR^+$, $-NR_2^+$, cyclic amine salts, pyridine salts, substituted pyridine salts, $PH_2^+$, $-PHR^+$, and $-PR_2^+$.

13. The method of claim 10 wherein said ionized moiety is nucleophilic.

14. The method of claim 13 wherein said nucleophilic moiety is selected from the group consisting of $-S^-$, $-O^-$, $-NH^-$, $-N(alkyl)^-$, $-N(aryl)^-$, $N(acyl)^-$, $-COO^-$, $-C(=S)O^-$, $-C(=S)S^-$, $-C(=O)S^-$, $-P(=O)O_2^-$, $-P(=O)O_2H^-$, and $-S(=O)_2O^-$.

15. The method of claim 10 wherein said sensing functional group is selected from the group consisting of SH, OH, $NH_2$, NH-alkyl, NH-aryl, NH-acyl, unsaturated hydrocarbon or substituted hydrocarbon, heterocyclic systems, carboxylic acid and its derivatives, sulfuric acid and its derivatives, and phosphoric acid and its derivatives.

16. The method of claim 10 wherein each working electrode is independently selected from the group consisting of single metals, metal alloys, metal oxides, organic-semiconducting materials, and inorganic-semiconducting materials.

17. The method of claim 16 wherein each working electrode is selected from the group consisting of Pt, Au, Ag, Cu, Si, GaAs, InP, $In_2O_3$, and ZnO.

18. The method of claim 10 wherein said reference electrode forms electrode pairs with at least some of said working electrodes and is chemically inert toward said ionized moiety.

19. The method of claim 10 wherein said coating is selectively deposited by the following process:
selectively activating one of the working electrodes;
pre-ionizing an ionizable moiety of said sensing element to form the ionized moiety;
performing an electric-field directed deposition of said sensing element onto the one electrode; and
post-cleaning said array.

20. A method of sensing a plurality of detectable functional groups associated with at least one of chemical moieties and biological moieties on a single molecule, said method comprising:
providing a sensor array, said sensor array comprising a plurality of working electrodes electrically associated with a single reference electrode, each working electrode forming a transducer, each working electrode selectively deposited with a coating of a sensing element comprised of an ionized moiety and a sensing functional group sensitive to at least one of said chemical and biological moieties on the single molecule, each coating sensitive to a different detectable functional group, each coating provided by performing an electric-field directed deposition of said sensing element onto said electrode, wherein the selective deposition of the coating on each working electrode is accomplished via one electrode at a time by activating one working electrode to be coated while deactivating each other of the working electrodes;

exposing said sensor array to at least one the chemical moiety or the biological moiety or both; and detecting a signal corresponding to a sensed chemical moiety or a sensed biological moiety or both.

21. The method of claim 20 wherein said ionized moiety is electrophilic.

22. The method of claim 21 wherein said electrophilic moiety is selected from the group consisting of $—NH_2^+$, $—NHR^+$, $—NR_2^+$, cyclic amine salts, pyridine salts, substituted pyridine salts, $PH_2^+$, $—PHR^+$, and $—PR_2^+$.

23. The method of claim 20 wherein said ionized moiety is nucleophilic.

24. The method of claim 23 wherein said nucleophilic moiety is selected from the group consisting of $—S^-$, $—O^-$, $—NH^-$, $—N(alkyl)^-$, $—N(aryl)^-$, $N(acyl)^-$, $—COO^-$, $—C(=S)O^-$, $—C(=S)S^-$, $—C(=O)S^-$, $—P(=O)O_2^-$, $—P(=O)O_2H^-$, and $—S(=O)_2O^-$.

25. The method of claim 20 wherein said sensing functional group is selected from the group consisting of SH, OH, $NH_2$, NH-alkyl, NH-aryl, NH-acyl, unsaturated hydrocarbon or substituted hydrocarbon, heterocyclic systems, carboxylic acid and its derivatives, sulfuric acid and its derivatives, and phosphoric acid and its derivatives.

26. The method of claim 20 wherein each working electrode is independently selected from the group consisting of single metals, metal alloys, metal oxides, organic-semiconducting materials, and inorganic-semiconducting materials.

27. The method of claim 26 wherein each working electrode is selected from the group consisting of Pt, Au, Ag, Cu, Si, GaAs, InP, $In_2O_3$, and ZnO.

28. The method of claim 20 wherein said reference electrode forms electrode pairs with at least some of said working electrodes and is chemically inert toward said ionized moiety.

* * * * *

UNITED STATES PATENT AND TRADEMARK OFFICE
CERTIFICATE OF CORRECTION

PATENT NO. : 7,780,841 B2
APPLICATION NO. : 11/059258
DATED : August 24, 2010
INVENTOR(S) : Sean Xiao-An Zhang et al.

Page 1 of 1

It is certified that error appears in the above-identified patent and that said Letters Patent is hereby corrected as shown below:

In column 11, line 9, in Claim 20, delete "one the" and insert -- one of the --, therefor.

Signed and Sealed this
Eighth Day of March, 2011

David J. Kappos
*Director of the United States Patent and Trademark Office*